(12) United States Patent
Doerr et al.

(10) Patent No.: US 8,126,540 B2
(45) Date of Patent: Feb. 28, 2012

(54) SINGLE CHAMBER CARDIAC STIMULATOR

(75) Inventors: Thomas Doerr, Berlin (DE); Ulrich Tietze, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 333 days.

(21) Appl. No.: 12/573,798

(22) Filed: Oct. 5, 2009

(65) Prior Publication Data

US 2010/0114212 A1   May 6, 2010

(30) Foreign Application Priority Data

Nov. 4, 2008  (DE) .................... 10 2008 043 450

(51) Int. Cl.
*A61N 1/00* (2006.01)
(52) U.S. Cl. .......................... 600/518; 607/5
(58) Field of Classification Search ............. 607/4–28; 600/508–523
See application file for complete search history.

(56) References Cited

U.S. PATENT DOCUMENTS

| 2005/0192505 | A1 | 9/2005 | Ostroff |
| 2006/0247703 | A1 | 11/2006 | Gutierrez |

FOREIGN PATENT DOCUMENTS

DE   102005049009   4/2007

OTHER PUBLICATIONS

German Search Report, dated Jul. 14, 2009, 2 pages.

*Primary Examiner* — Scott Getzow
(74) *Attorney, Agent, or Firm* — ARC IP Law, PC; Joseph J. Mayo (57) ABSTRACT

A single-chamber cardiac stimulator (10) with at least partially electrically conductive housing (12) and first detection unit (52) connected via a ventricular electrode line to at least one ventricular electrode and another electrode and configured to record ventricular cardiac activity with first electrocardiogram signal via the ventricular electrode and additional electrode, comprises a second detection unit (70), connected via the ventricular electrode line to at least one electrode of the ventricular electrode line and is connected to another electrode and configured to record a second electrocardiogram signal simultaneously with the first electrocardiogram signal via these electrodes, such that at least one of the two electrodes by means of which the second electrocardiogram signal is to be recorded is another electrode by means of which the first electrocardiogram signal is to be recorded, so that the electrocardiogram signals form ECG leads whose vectors are not equal to 0° or 180°.

12 Claims, 6 Drawing Sheets

SINGLE CHAMBER CARDIAC STIMULATOR

This application takes priority from German Patent Application DE 10 2008 043 450.7, filed 4 Nov. 2008, the specification of which is hereby incorporated herein by reference.

BACKGROUND OF THE INVENTION

1. Field of the Invention

Embodiments of the invention relate to a single-chamber cardiac stimulator, in particular an implantable cardiac pacemaker or an implantable cardioverter/defibrillator, with a right-ventricular electrode line. At least one right-ventricular sensing electrode and one right-ventricular stimulation electrode are attached to this electrode line; in the individual case, these electrodes may also be formed by a single electrode pole, which then serves as both the stimulation electrode and as the sensing electrode.

2. Description of the Related Art

A single-chamber cardiac stimulator is understood here to refer to a cardiac stimulator, which in the usual nomenclature is capable of recording an intracardiac electrocardiogram via a corresponding sensing electrode in only one chamber of the heart and delivering stimulation pulses only to this ventricle via a corresponding stimulation electrode. The stimulation electrode and the sensing electrode may be different from one another or may be formed by the same electrode pole. A single-chamber cardiac stimulator should also be understood here to refer to a cardiac stimulator, which may essentially also be connected to sensing electrodes in multiple chambers of the heart and thus may serve as a multi-chamber cardiac stimulator, but during operation the latter is connected only to an electrode line for sensing and/or for stimulation in a cardiac chamber.

One advantage of such a single-chamber cardiac stimulator is its fundamentally simple design combined with the fact that only a single electrode line need be implanted in a patient's heart.

There are various algorithms for discriminating between ventricular tachycardias (VT) and supraventricular tachycardias (SVT). None of the algorithms that require information about the atrial rhythm can be used for single-chamber ICDs. For these single-chamber ICDs, the sudden onset of tachycardia and the RR interval stability are established criteria for VT/SVT discrimination. In addition, these criteria are supplemented by an evaluation of the QRS complex morphology. However, these morphology-based algorithms have only limited suitability because the QRS morphology, derived in just one ECG lead in a VT, can be represented as unchanged in comparison with sinus rhythm. In these cases, a VT would be wrongly classified as an SVT and therefore would not be treated.

Figure 6:
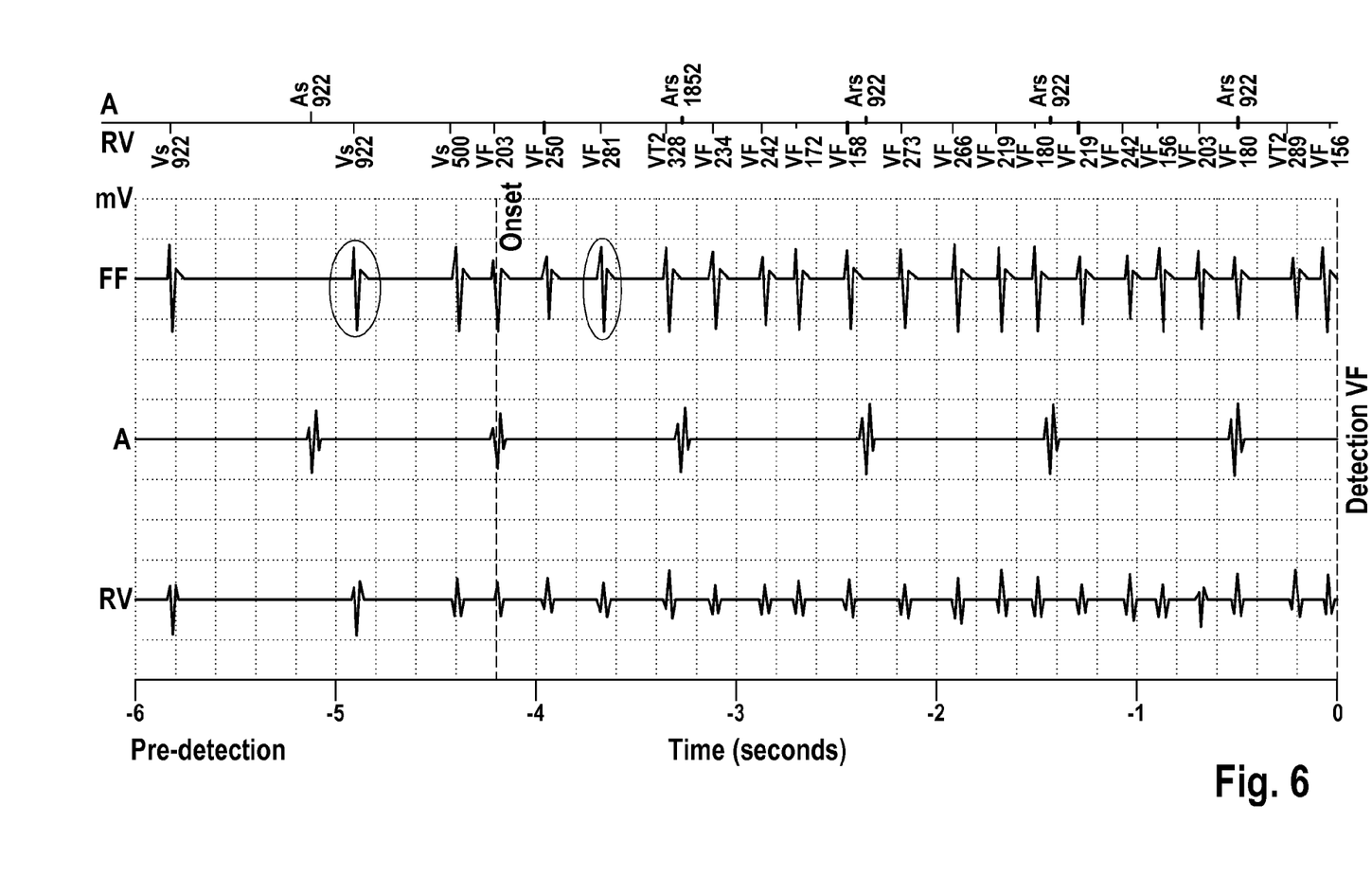
FIG. 6: shows a comparison of various electrocardiograms.

FIG. 6 illustrates such an example. This diagram shows the ECG before and during a ventricular tachycardia. In the channel labeled as FF, the far-field ECG lead between the ventricular shock electrode and the housing of the ICD is shown. The two marked QRS complexes show the QRS morphology in sinus rhythm and during a ventricular tachycardia. It can be seen clearly here that the morphologies are the same and thus do not constitute a basis for discrimination.

BRIEF SUMMARY OF THE INVENTION

The object of the one or more embodiments of the invention is to create a cardiac stimulator that will allow an improved VT/SVT discrimination.

According to embodiments of the invention, this object is achieved by a cardiac stimulator having an at least partially electrically conductive housing, a first detection unit for detecting a first electrocardiogram signal (first channel), a second detection unit for simultaneous detection of a second electrocardiogram signal (second channel), a morphology evaluation unit and a VT/SVT discrimination unit. The first detection unit is connected or connectable to at least one ventricular electrode and one other electrode via a ventricular electrode line and is designed to detect ventricular cardiac activity by means of a first electrocardiogram signal via the ventricular electrode and the additional electrode. The second detection unit is, on the one hand, connected or connectable via the ventricular electrode line to at least one electrode of this ventricular electrode line and, on the other hand, is connected to another electrode and is designed to record a second electrocardiogram signal simultaneously with the first electrocardiogram signal via these electrodes, such that at least one of the two electrodes by means of which the second electrocardiogram signal is to be recorded is another electrode by means of which the first electrocardiogram signal is to be recorded, so that the electrocardiogram signals are ECG leads whose vectors are not equal to 0° or 180°.

The morphology evaluation unit is designed for determining at least one morphological signal characteristic of the first electrocardiogram signal and of the simultaneous second electrocardiogram signal in a second ECG channel. The VT/SVT discrimination unit is connected to the morphology evaluation unit and is designed to utilize the signal characteristics determined by the morphology evaluation unit for VT/SVT discrimination.

It is assumed in one or more embodiments of the invention that a change in ECG morphology in comparison with a sinus rhythm is represented in two ECG leads (derived in non-parallel projections) with a VT in at least one lead.

FIG. 6 shows a change in signal morphology in the right-ventricular IEGM (RV).

The first detection unit is preferably a ventricular sensing unit, which is connected or connectable to at least one pair of ventricular sensing electrodes via a ventricular electrode line. Such a pair of ventricular sensing electrodes may be formed by a ventricular tip electrode and a neighboring ring electrode, for example. The ventricular sensing unit as the first detection unit is preferably designed to record the first electrocardiogram signal as a bipolar electrocardiogram signal via this electrode pair and to detect and classify ventricular cardiac activity in a known way by means of the first electrocardiogram signal, which is recorded as with bipolar leads, i.e., to detect ventricular cardiac activity.

The second detection unit is, on the one hand, connected or connectable via the ventricular electrode line to at least one defibrillation electrode of this ventricular electrode line and, on the other hand, to the electrically conductive housing of the single-chamber cardiac stimulator as an additional electrode. A defibrillation electrode is usually designed as a shock coil and has a much larger surface area in comparison with typical stimulation electrodes or sensing electrodes. The second detection unit is preferably designed to record the second electrocardiogram signal as a far-field electrocardiogram signal by means of these two electrodes—a shock coil of the ventricular electrode line and the conductive housing of the stimulator.

Alternatively, the second detection unit may also be connected or connectable to two defibrillation electrodes (i.e., shock coils) on this electrode line via the ventricular electrode line. In this case, the second detection unit is designed to record the second electrocardiogram signal as a far-field electrocardiogram signal with these two defibrillation electrodes.

The VT/SVT discrimination unit is preferably designed to determine the ratio of mutually assigned signal characteristics determined by the morphology evaluation unit and to compare them with at least one first reference ratio value. The signal characteristics may be, for example, the peaks of the respective QRS complex detected. The ratio of the peaks of corresponding QRS complexes of the two electrocardiogram signals recorded in parallel is formed and compared with at least one reference ratio value.

The cardiac stimulator is preferably also a time measuring unit, which makes it possible to determine the duration of the prevailing RR intervals and/or the inverse, i.e., the prevailing ventricular rate, and to send the value thereby determined to the VT/SVT discrimination unit. The VT/SVT discrimination unit is in this case designed to compare a particular RR interval or the corresponding ventricular rate with at least one VT zone limit value, and for the case when the RR interval is shorter than the VT zone limit value or the ventricular rate is greater than the VT zone limit value, to form a ratio obtained from the prevailing signal characteristics determined by the morphology evaluation unit and assigned to one another and to compare this ratio with the reference ratio value.

Furthermore, the VT/SVT discrimination unit is preferably designed to save as the reference ratio the ratio of the mutually assigned signal characteristics, which were determined by the morphology evaluation unit and recorded during a normal rhythm. The VT/SVT discrimination unit dictates a normal rhythm when a respective RR interval is longer than a corresponding VT zone limit value or a respective ventricular rate is lower than a corresponding VT zone limit value.

The time measuring unit is preferably designed to determine a particular RR interval or its inverse, the ventricular rate, over several successive cardiac cycles and to send the value thereby determined to the VT/SVT discrimination unit.

To facilitate not only differentiation between normal rhythm and tachycardia but also detection of fibrillation, which is usually characterized by even higher heart rates than those occurring in tachycardia, the VT/SVT discrimination unit is preferably designed to compare a particular RR interval or the ventricular rate not only with a first VT zone limit value but also with a second VT zone limit value. The two VT zone limit values form an upper limit and a lower limit of a tachycardia zone. If the ventricular rate is above the upper limit (second VT zone limit value) of the VT zone, the VT/SVT discrimination unit will detect a ventricular fibrillation.

In addition, it is preferable if the morphology evaluation unit is designed to determine a particular signal characteristic, including the respective plus or minus sign of the signal amplitude of the respective electrocardiogram signal, and to send it to the VT/SVT discrimination unit.

In addition, the morphology evaluation unit is preferably designed to determine a particular signal characteristic within a time slot extending over a period of time beginning a predetermined amount of time before a particular detected ventricular cardiac activity and ending at a point in time after the detected ventricular cardiac activity by a certain amount of time. The morphology evaluation unit here is preferably connected to the ventricular sensing unit, which is designed to detect ventricular cardiac activity and send the point in time of a detected ventricular cardiac activity to the morphology evaluation unit.

Additional advantageous embodiments of the invention are derived from the combination of the advantageous features described here as well as the features mentioned in the following description of an exemplary embodiment.

BRIEF DESCRIPTION OF THE DRAWINGS

The invention will now be explained in greater detail on the basis of an exemplary embodiment with reference to the figures, in which.

DETAILED DESCRIPTION OF THE INVENTION

Figure 1:
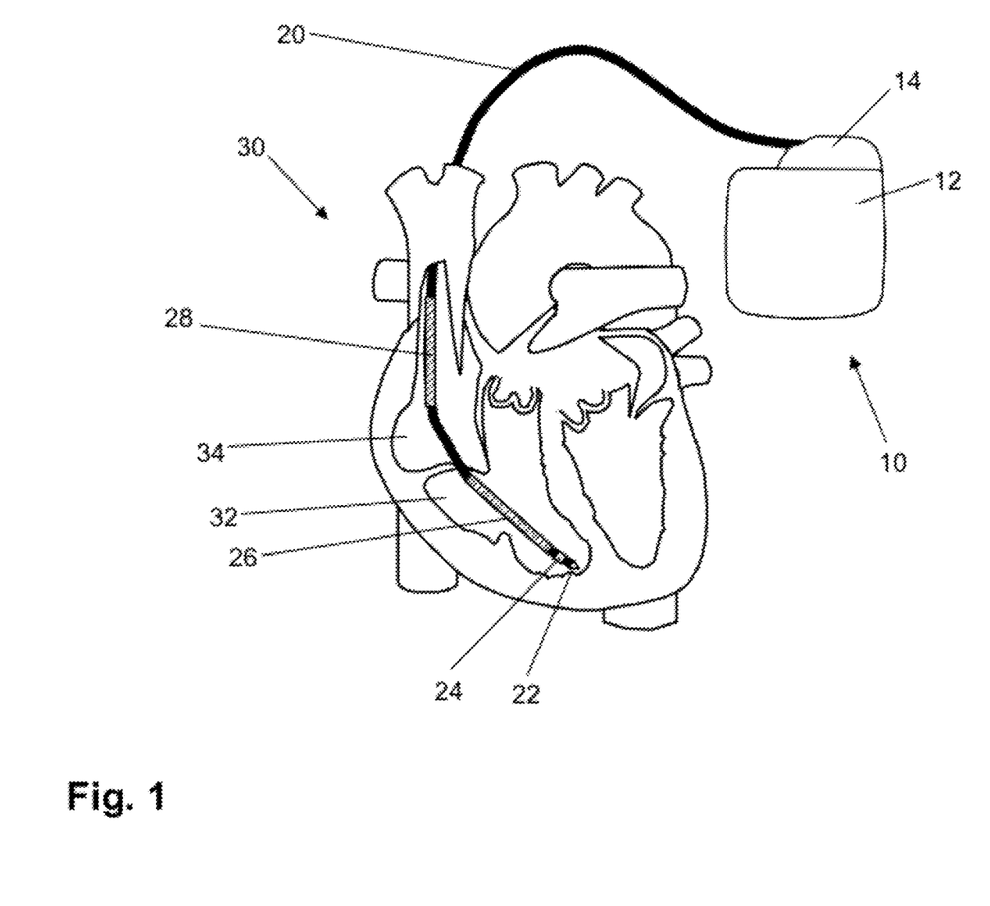
FIG. 1: shows a cardiac stimulator in the form of an implantable single-chamber cardioverter/defibrillator in combination with electrode lines connected thereto.

FIG. 1 shows a ventricular cardiac stimulator 10 with a housing 12 and a header 14. The housing 12 is hollow and has at least partially an electrically conductive surface; the housing 12 is typically made of a biocompatible metal such as titanium. The housing 12 holds a battery and electronic components of the cardiac stimulator 10. The header 14 has terminal bushings, e.g., for an electrode line.

FIG. 1 shows the cardiac stimulator 10 connected to a flexible implantable electrode line 20.

The electrode line 20 illustrated here is a ventricular electrode line having a ventricular tip electrode 22 and a ventricular ring electrode 24 on its distal end, together forming a bipolar detection pole and stimulation pole. Of these, the ventricular tip electrode 22 serves as a stimulation electrode. The ventricular tip electrode 22 and the ventricular ring electrode 24 together form an electrode pair for bipolar sensing of ventricular events. To do so, the ventricular tip electrode 22 and the ventricular ring electrode 24 are connected to a ventricular stimulation unit and a ventricular sensing unit in the interior of the housing 12 of the cardiac stimulator 10 (further details are described in conjunction with FIG. 2). Furthermore, the ventricular electrode line 20 has a ventricular shock coil 26 as a distal shock coil and a proximal shock coil 28. The ventricular shock coil 26 is arranged on the ventricular electrode line 20 in such a way that, when inserted into the heart 30, it is in the right ventricle 32 of the heart. The ventricular tip electrode 22 is then at the apex of the ventricle 32 of the heart 30. The proximal shock coil 28 is in the superior vena cava of the heart 30 when the ventricular electrode line 20 is implanted. No special electrode line is provided for stimulation of the right atrium 34 of the heart 30. Likewise there is no atrial sensing electrode. The cardiac stimulator 10 does not use an atrial electrode line at all and nevertheless offers the functionality of cardiac stimulators which are connected to an atrial electrode line. This is explained in greater detail below.

Figure 2:
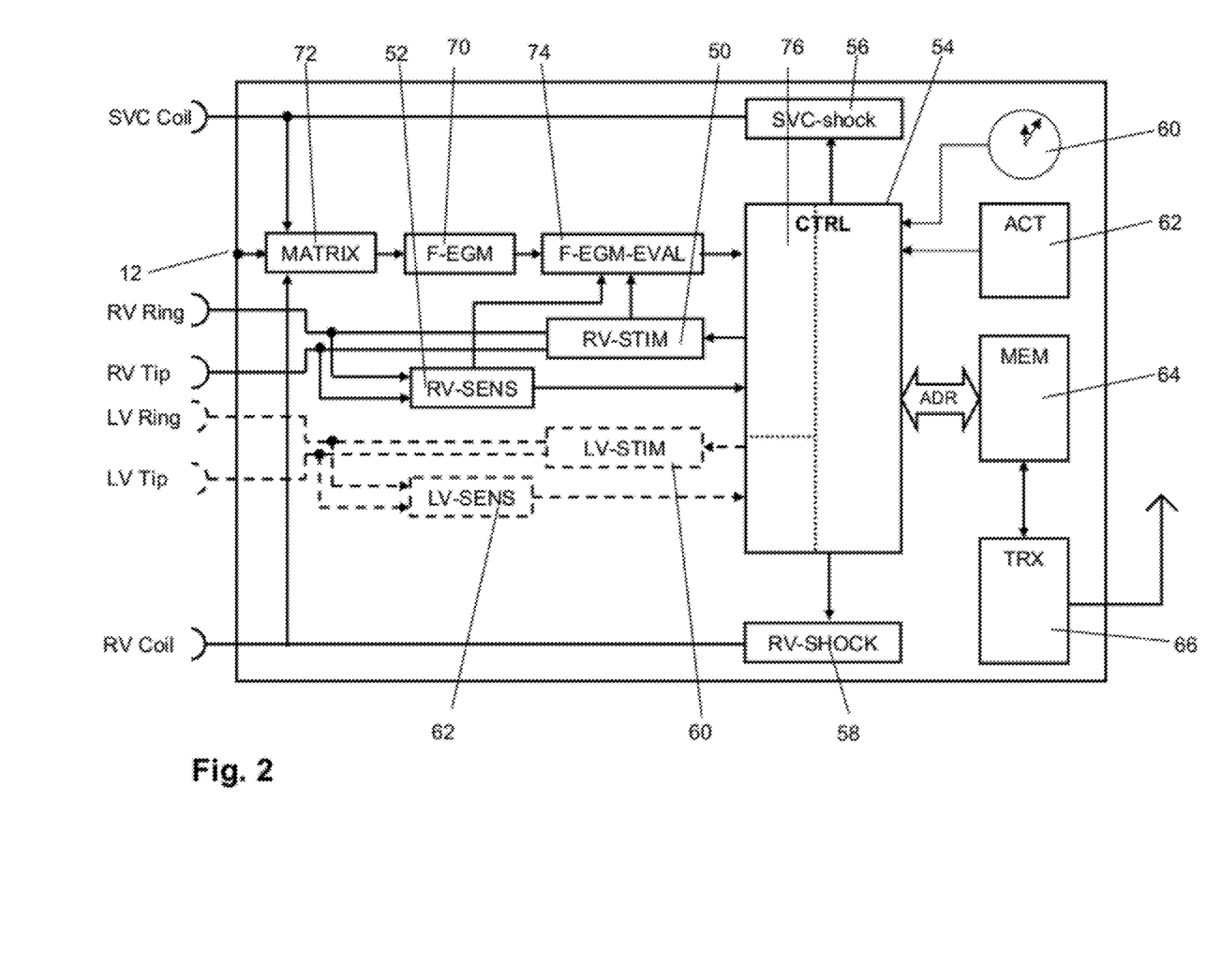
FIG. 2: shows a schematic block diagram of a cardiac stimulator from FIG. 1.

FIG. 2 shows in a schematic block diagram the components of the cardiac stimulator 10, which are arranged in the interior of the housing 12. This diagram is not necessarily definitive. In particular, components shown with dotted lines in FIG. 2 are not implemented in the cardiac stimulator 10 from FIG. 1.

As already indicated, the cardiac stimulator 10 has terminal contacts in its header 14 for connecting the corresponding mating contacts of an electrode line plug on the proximal end of the electrode line 20. These contacts serve to provide an electric connection to the electrodes of the electrode line 20. The proximal shock coil 38 is thus connected to the contact SVC coil, the ventricular (distal) shock coil 26 is connected to the terminal RV coil, the right-ventricular tip electrode 22 is connected to the terminal RV tip and the right-ventricular ring electrode is connected to the terminal RV ring. The right-ventricular tip electrode 22 and the right-ventricular ring electrode 24 are each connected to a right-ventricular stimulation unit 50 and a right-ventricular sensing unit 52 via the terminals RV tip and RV ring. The right-ventricular sensing unit 52 is connected at the output to a stimulation unit 54 which in turn has an output connected to the right-ventricular stimulation unit 50. The right-ventricular stimulation unit 50 is designed to generate a ventricular stimulation pulse in response to a corresponding control signal of the stimulation control unit 54 and to deliver it via at least the contact RV tip.

The functioning of the right-ventricular sensing unit 52 is explained in greater detail below with reference to FIGS. 3 and 4. The right-ventricular sensing unit is fundamentally designed to analyze the course of a signal derived from the difference in the potentials applied to the terminals RV tip and RV ring. This signal characteristic typically has signal peaks which occur in the event of ventricular depolarizations. Ventricular depolarizations precede contraction of the ventricular myocardium and thus characterize ventricular sensing events. These can be detected from the signal characteristic by comparing the potentials with a threshold value, which is set so that signal peaks associated with ventricular depolarization exceed the threshold value, so the ventricular sensing unit 52 can detect ventricular sense events by threshold value comparison when the threshold value is exceeded.

To generate and deliver defibrillation shocks, shock generators 56 and 58 are also connected via the terminal SVC coil to the proximal shock coil 28 and/or connected via the terminal RV coil to the distal shock coil 26. The two defibrillation shock generators 56 and 58 are also each connected to the stimulation control unit 54. Additional features of the cardiac stimulator 10 include a timer 60, which is used for interval measurement and heart rate determination, for example, and an activity sensor 62 designed to detect a patient's physical activity, e.g., by motion detection, to enable the stimulation control unit 54 to adjust a stimulation rate to the physiological needs of the patient. In addition, the cardiac stimulator 10 has a memory 64 for storing control parameters and physiological parameters obtained, e.g., by analyzing the various signals recorded by the cardiac stimulator 10.

Finally, the cardiac stimulator 10 also has a telemetry unit 66 by means of which the cardiac stimulator 10 can wirelessly transmit physiological parameters obtained and saved to an external device or by means of which the cardiac stimulator 10 can receive control parameters to control the functioning of the cardiac stimulator 10.

In the sense of the present invention, the cardiac stimulator 10 also has, on the one hand, a far-field electrocardiogram detection unit 70 connected at the input end to a switching matrix 72 by means of which the far-field electrocardiogram detection unit 70 is optionally connected to different electrode poles.

Essentially the following electrode configurations are obtained for the input signal of the far-field electrocardiogram detection unit 70:

|  | first ECG | second ECG |
|---|---|---|
| Variant A: | RV coil - housing | SVC coil - housing |
| Variant B: | RV coil - housing | SVC coil - coil |
| Variant C: | SVC coil - housing | SVC coil - coil |
| Variant D: | RV tip - RV ring | RV coil - housing |

All these combinations yield ECG vectors that do not run parallel to one another.

However, variant D is to be preferred because it does not have a "dual-coil" electrode as a prerequisite for VT/SVT discrimination. Therefore, the following implementation examples are limited to this preferred combination.

Since several electrode configurations are possible for determination of the ECG leads, the switching matrix 72 is provided in the exemplary embodiment; it can either be programmed manually by the user or the best lead in each case can be selected automatically on the basis of electrode impedances and signal quality.

The potential difference between the two selected inputs yields a far-field electrocardiogram, which is recorded by the far-field electrocardiogram detection unit 70, amplified, converted analog-to-digital and filtered as explained in greater detail with reference to FIG. 3. The far-field electrocardiogram obtained and processed in this way is applied to an output of the far-field electrocardiogram detection unit 70. This output is connected to an input of a far-field electrocardiogram evaluation unit 74. This far-field electrocardiogram evaluation unit 74 also has one input connected to the right-ventricular sensing unit 52 and another input connected to the right-ventricular stimulation unit 50. As an alternative, a single input of the far-field electrocardiogram evaluation unit 74, connected to the stimulation control unit 54, may also be provided. These additional inputs of the far-field electrocardiogram evaluation unit 74 serve to supply signals characterizing the ventricular sensing events and/or ventricular stimulation events to the far-field electrocardiogram evaluation unit 74. The far-field electrocardiogram evaluation unit 74 is designed to evaluate the far-field electrocardiogram formed by the far-field electrocardiogram detection unit 70, taking into account ventricular signals that characterize sensing events and stimulation events, to detect signal features characterizing the atrial (sensing) events in the far-field electrocardiogram.

Far-field electrocardiogram evaluation unit 74 is connected at the output to a VT/SVT discrimination unit 76 as part of the stimulation control unit 54. The VT/SVT discrimination unit 76 contains a morphology evaluation unit, which is designed to determine at least one certain signal characteristic such as the maximum amplitude of a particular QRS complex of the electrocardiograms recorded by the ventricular sensing unit 52 and the far-field electrocardiogram detection unit 70. This is explained in greater detail below.

Figure 3:
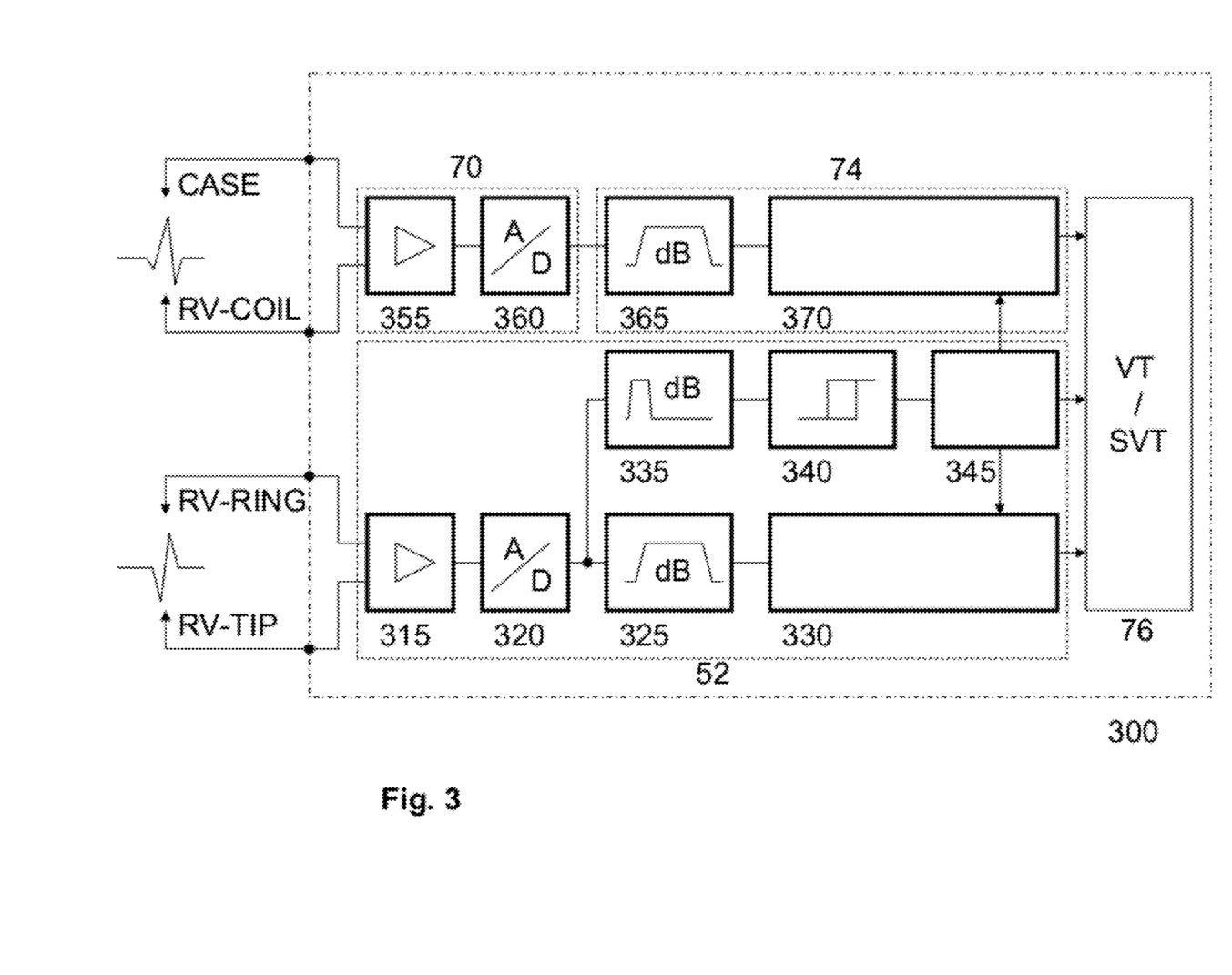
FIG. 3: shows the components of the cardiac stimulator provided for VT/SVT discrimination from FIGS. 1 and 2 in a detailed diagram.

FIG. 3 shows a block diagram with the components of a single-chamber ICD shown as a cardiac stimulator producing an inventive VT/SVT discrimination.

The ICD is connected via the terminals RV tip and RV ring to the bipolar sensing and stimulation electrode line 20. The intracardiac electrogram (IEGM) derived by electrodes 22 and 24 of this electrode line 20 is first amplified by an amplifier 315 and digitized by an A-D converter 320. Next the digital signal thereby obtained is sent to a narrow-band filter stage 335. This narrow-band filter stage 335, e.g., a second-order band-pass filter from 20 Hz to 40 Hz serves to filter the IEGM for the ventricular sensing function, as is customary in an ICD. Then in an adaptive comparator stage 340 the sensing (detection) of the ventricular events (sensing) is performed, e.g., by threshold value comparison. In a downstream time measuring unit 345, the intervals of time between successive ventricular events (RR intervals) are determined and classified, e.g., assigned to different tachycardia zones.

In parallel with the usual sensing function of the ventricular IEGM, the digitized IEGM signal is sent to a second parallel broad-band filter stage 325. The filter characteristic used here is optimized to obtain the largest possible spectral component of the QRS morphology but still eliminate most interference signals. This broad-band filter stage 325 is connected to a unit 330 for determining the maximum amplitude of the QRS complex. This unit 330 has a ring memory in which the IEGM can be stored temporarily for a period of 50 ms to 250 ms. The QRS maximum is always determined in this unit 330 by being triggered by a ventricular event. This trigger is made available by the time measuring unit 345. If the unit 330 is triggered, it determines the maximum IEGM amplitude in the time environment of the trigger point in time, e.g., 100 ms before to 100 ms after the trigger point in time, depending on the plus or minus sign.

The QRS maximum amplitude of the first electrocardiogram signal determined in this way is supplied to the VT/SVT discrimination unit 76.

Another ECG lead is provided between the distal shock coil 26 via the terminal RV shock and the housing 12 of the ICD (via the terminal CASE). A far-field electrocardiogram derived in this way as a second electrocardiogram signal is also amplified by an amplifier 355 and digitized by a second A-D converter 360, broad-band filtered by means of a filter stage 365 and sent to another unit 370 for determination of the QRS maximum. The QRS maximum is determined as done in the first channel (by the unit 330). The maximum values thus determined in the second electrocardiogram signal are also relayed to the VT/SVT discrimination unit 76.

The VT/SVT discrimination unit 76 also receives the RR intervals classified by the time measuring unit 345.

Figure 4:
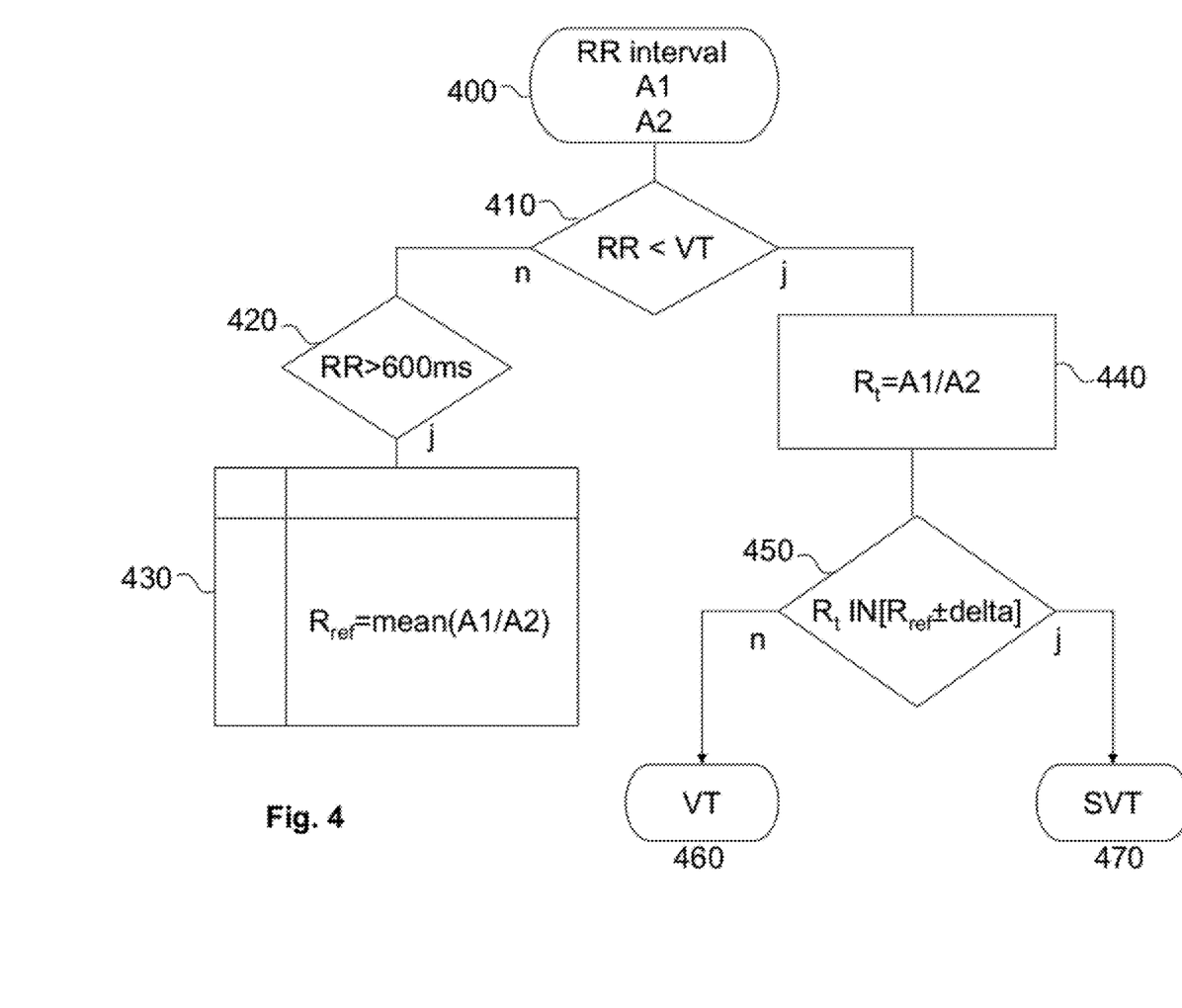
FIG. 4: shows the operation of the VT/SVT discrimination unit on the basis of a flow chart.

FIG. 4 illustrates the operation of the VT/SVT discrimination unit 76 from FIG. 3. The current RR interval and the QRS signal maximum of the first electrocardiogram signal (A1) and of the second electrocardiogram signal (A2) are made available (400) to the VT/SVT discrimination unit 76 with each ventricular event.

First, it checks on whether the current RR interval is within a VT zone (410). If this is not the case, it checks on whether the RR interval is greater than 600 ms (420). If this is the case, then the VT/SVT discrimination unit 76 calculates a reference value for the ratio of the QRS maximum amplitudes Rref (430), where this reference value typically corresponds to the median of several QRS complexes measured in succession.

However, if the current RR interval is within a VT zone (410), then a ratio of the QRS maximum amplitudes for the current interval is calculated (440). Next, three is a check of whether this value (Rt) corresponds to the reference value (Rref) plus a tolerance (delta). If this is the case, then the current RR interval is counted as an SVT (470); otherwise it is counted as a VT (460).

Figure 5:
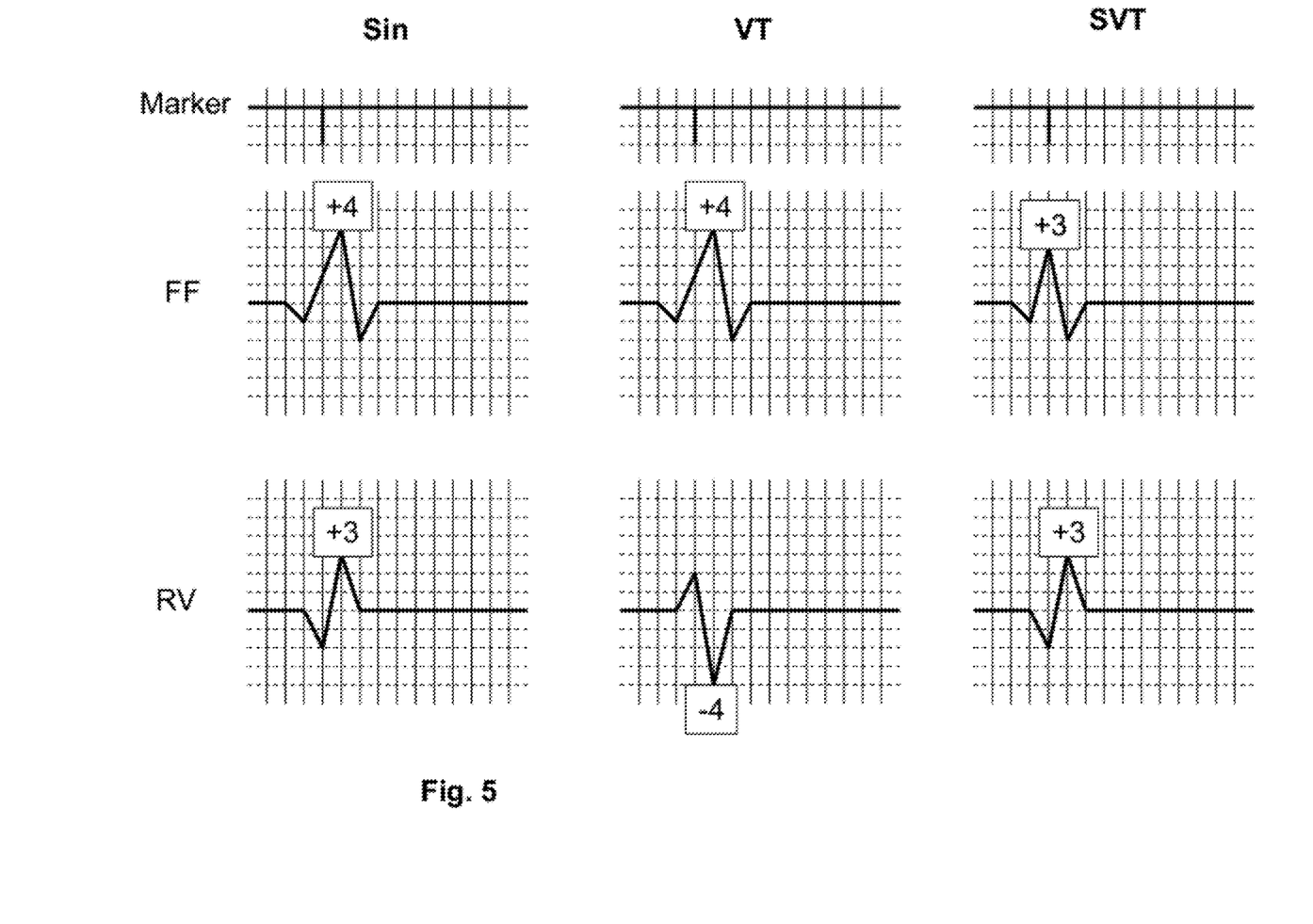
FIG. 5: shows the inventive 2-channel morphology evaluation on the basis of an example.

FIG. 5 shows the 2-channel morphology evaluation as an example. The marker line indicates the point in time of the ventricular event detected and thus indicates the trigger for the morphology analysis. The FF line indicates the respective signal morphology in the far-field channel, and the RV line indicates the morphology in the bipolar right-ventricular IEGM channel.

The Sin column shows an example with sinus rhythm. The VT column shows an example of a tachycardia, which has a change in morphology in only one of the two channels (as in FIG. 1) and the SVT column shows the example of a supraventricular tachycardia.

The VT/SVT discrimination unit 76 determines the reference value Rref in sinus rhythm in the example Rref=+4/+3=1.33.

If a VT is sensed, the event evaluation yields a value Rt=+4/−4=−1 (minus 1).

At a tolerance of delta=0.5, Rt is outside of [Rref−delta, Rref+delta] and is thus counted as VT.

If an SVT is sensed, the event evaluation yields a value Rt=+3/+3=1 (plus 1).

At a tolerance of delta=0.5, Rt is outside of [Rref−delta, Rref+delta] and is thus counted as SVT.

In addition to the maximum signal amplitude, other morphology criteria for the discrimination described in the exemplary embodiment can be used either individually or in combination (e.g., QRS width, integral of the area under the QRS complex, etc.).

The invention claimed is:

1. A single-chamber cardiac stimulator (10), comprising an at least partially electrically conductive housing (12);
    a ventricular electrode line comprising at least one electrode;
    at least one ventricular electrode;
    a second electrode;
    a third electrode;
    a first detection unit (52), which is connected via the ventricular electrode line to the at least one ventricular electrode and the second electrode wherein said first detection unit (52) is configured to record ventricular cardiac activity via a first electrocardiogram signal obtained via the at least one ventricular electrode and the second electrode;
    a second detection unit (70), which is connected via the ventricular electrode line to the at least one electrode of the ventricular electrode line and connected to the third electrode wherein said second detection unit (70) is configured to record a second electrocardiogram signal simultaneously with the first electrocardiogram signal via these electrodes, such that at least one of these electrodes, through which the second electrocardiogram signal is recorded, is another electrode through which the first electrocardiogram signal is recorded, so that the first and second electrocardiogram signals constitute electrocardiogram leads whose vectors are not equal to 0° or 180°;
    a morphology evaluation unit which is connected to the first and second detection units and is configured to determine at least one morphological signal characteristic of the first electrocardiogram signal and of the simultaneously recorded second electrocardiogram signal;
    a VT/SVT discrimination unit (76), which is connected to or comprises the morphology evaluation unit and is configured to utilize the at least one morphological signal characteristic determined by the morphology evaluation unit for ventricular tachycardias and supraventricular tachycardias discrimination; and,
    wherein the VT/SVT discrimination unit is configured to determine a ratio of signal characteristics as determined by the morphology evaluation unit and to compare said ratio with at least one first reference ratio value.

2. The single-chamber cardiac stimulator according to claim 1, wherein the first detection unit is a ventricular sensing unit, which is connected via the ventricular electrode line to at least one ventricular sensing electrode pair selected from said at least one ventricular electrode and is configured to record the first electrocardiogram signal via the at least one ventricular sensing electrode pair as a bipolar electrocardiogram signal and to sense the ventricular cardiac activity via the first electrocardiogram signal, recorded by bipolar leads, and to classify or detect the ventricular cardiac activity.

3. The single-chamber cardiac stimulator according to claim 1, wherein the second detection unit is connected via the ventricular electrode line to at least one defibrillation electrode or shock coil of the ventricular electrode line and is also connected to the at least partially electrically conductive housing (12) of the single-chamber cardiac stimulator as an additional electrode and is configured to record the second electrocardiogram signal as a far-field electrocardiogram signal via these two electrodes.

4. The single-chamber cardiac stimulator according to claim 1, wherein the second detection unit is connected via the ventricular electrode line to two defibrillation electrodes or shock coils of the ventricular electrode line and is configured to record the second electrocardiogram signal as a far-field electrocardiogram signal via these two defibrillation electrodes or shock coils.

5. The single-chamber cardiac stimulator according to claim 1 wherein the VT/SVT discrimination unit is configured to compare the ratio of mutually assigned signal characteristics determined by the morphology evaluation unit with a tolerance range around the at least one first reference ratio value, and if this ratio exceeds the tolerance range, to detect a ventricular tachycardia, and if this ratio is below the tolerance range, to detect a supraventricular tachycardia or vice versa.

6. The single-chamber cardiac stimulator according to claim 1, wherein
  the single-chamber cardiac stimulator has a time measuring unit (345) which is configured to determine a period of time between successive ventricular cardiac activity as a respective RR interval or its inverse as a respective ventricular rate and to send the respective RR interval or its inverse thereby determined to the VT/SVT discrimination unit (76); and,
  the VT/SVT discrimination unit (76) is configured to compare a particular RR interval or a particular ventricular rate with at least one VT zone limit value and for a case when the respective RR interval is shorter than a corresponding VT zone limit value or the respective ventricular rate is larger than the corresponding VT zone limit value, to determine a respective ratio of current mutually assigned signal characteristics determined by the morphology evaluation unit to one another and to compare this ratio with at least the at least one first reference ratio value.

7. The single-chamber cardiac stimulator according to claim 6, wherein the VT/SVT discrimination unit (76) is configured to save as the at least one reference ratio value a ratio of mutually assigned signal characteristics determined by the morphology evaluation unit for the case when the respective RR interval is longer than the corresponding VT zone limit value, or the respective ventricular rate is lower than the corresponding VT zone limit value.

8. The single-chamber cardiac stimulator according to claim 6 wherein the time measuring unit (345) is configured to average the respective RR interval or its inverse as the respective ventricular rate over several successive cardiac cycles and to send the respective RR interval thereby determined or its inverse as the respective ventricular rate to the VT/SVT discrimination unit (76).

9. The single-chamber cardiac stimulator according to claim 5 wherein the VT/SVT discrimination unit is configured to compare a respective RR interval or a respective ventricular rate with at least two VT zone limit values and to assign the respective RR interval or the respective ventricular rate to a VT zone when the respective RR interval is shorter than a first VT zone limit value and is longer than a second VT zone limit value and/or the respective ventricular rate is higher than the first VT zone limit value and is lower than the second VT zone limit value, and to assign the respective RR interval or the respective ventricular rate to the VT zone when the respective RR interval is shorter than the first and second VT zone limit values and/or the respective ventricular rate is greater than the first and second VT zone limit values.

10. The single-chamber cardiac stimulator according to claim 1 wherein the morphology evaluation unit is configured to determine a respective signal characteristic including a respective plus or minus sign of a signal amplitude of a respective electrocardiogram signal and to send the respective signal characteristic to the VT/SVT discrimination unit.

11. The single-chamber cardiac stimulator according to claim 1 wherein the morphology evaluation unit is configured to determine a respective signal characteristic within a time slot extending over a period of time beginning a predetermined amount of time before a respective detected ventricular cardiac activity and ending at a point in time after a detected ventricular cardiac activity by a second predetermined amount of time.

12. The single-chamber cardiac stimulator according to claim 2 wherein the morphology evaluation unit is connected to the ventricular sensing unit which is configured to detect the ventricular cardiac activity and to send a point in time of a detected ventricular cardiac activity to the morphology evaluation unit.

* * * * *